United States Patent
Rutsky

(10) Patent No.: US 6,512,160 B1
(45) Date of Patent: Jan. 28, 2003

(54) INK PRINTABLE BANDAGES

(75) Inventor: Aaron D. Rutsky, Simsbury, CT (US)

(73) Assignee: Innova Corporation, Bloomfield, CT (US)

( * ) Notice: Subject to any disclaimer, the term of this patent is extended or adjusted under 35 U.S.C. 154(b) by 0 days.

(21) Appl. No.: 09/965,254

(22) Filed: Sep. 25, 2001

(51) Int. Cl.$^7$ .............................................. A61F 13/00
(52) U.S. Cl. .......................... 602/41; 602/42; 602/44; 602/54; 602/55; 602/900
(58) Field of Search .................. 602/41–47, 54–55, 602/60, 900

(56) References Cited

U.S. PATENT DOCUMENTS

| | | | |
|---|---|---|---|
| 3,616,156 A | | 10/1971 | Scholl |
| 4,126,130 A | | 11/1978 | Cowden et al. |
| D267,431 S | | 12/1982 | Santarelli |
| D267,432 S | | 12/1982 | Santarelli |
| 4,406,662 A | | 9/1983 | Beran et al. |
| D304,238 S | | 10/1989 | Palau |
| 5,088,484 A | | 2/1992 | Freeman et al. |
| D340,987 S | | 11/1993 | Arginsky |
| D340,989 S | | 11/1993 | Arginsky |
| 5,338,615 A | * | 8/1994 | Quick et al. |
| 5,342,291 A | * | 8/1994 | Scholz et al. |
| D368,526 S | | 4/1996 | Palermo |
| 5,702,356 A | | 12/1997 | Hathman |
| 5,725,488 A | | 3/1998 | Yoon et al. |
| D394,506 S | | 5/1998 | Prescott |
| D408,540 S | | 4/1999 | Dunshee et al. |
| 5,891,078 A | | 4/1999 | Turngren et al. |
| 5,981,823 A | | 11/1999 | Turngren |
| 6,042,912 A | * | 3/2000 | Simoni |
| D433,139 S | | 10/2000 | Brogden et al. |

* cited by examiner

Primary Examiner—Michael A. Brown
Assistant Examiner—Lalita M Hamilton
(74) Attorney, Agent, or Firm—McCormick, Paulding & Huber LLP

(57) ABSTRACT

A bandage is adapted to receive a printed graphic image which is printed by a personal home printer. The predetermined graphic image may be chosen from a graphics library loaded onto a personal computer, a graphic image designed by an operator or a graphic image downloaded from the internet. The bandage includes a first layer treated with a coating on one planar side, the coating bonding with the printed graphic image in a waterproof manner. The bandage further includes a second pressure sensitive adhesive layer disposed on another planar side of the first layer, and a third liner layer which overlays the second adhesive layer. The third liner layer is selectively removable from the second adhesive layer to expose the second adhesive layer.

8 Claims, 3 Drawing Sheets

INK PRINTABLE BANDAGES

FIELD OF THE INVENTION

This invention relates in general to ink printable bandages, and deals more particularly with ink printable bandages which permit fanciful graphics to be printed thereon, from a home computer or the like, whereby the ink utilized bonds with a coating on the bandages so as to be water insoluble.

BACKGROUND OF THE INVENTION

Over the years, many improvements have been made to bandages in order to create more sterile and effective dressings for wounds of all sizes. Recently, in association with technological improvements in bandage manufacture, there have also been efforts to increase their visual appeal to users, especially younger users, by adorning bandages, gauzes and cast mediums with colors or designs. These adornments, however, are limited to a relatively few designs chosen by the manufacturer and therefore may not be especially pleasing to all. Moreover, not all retail outlets carry these specialty bandages and so they may not be readily available to all consumers who may be desirous of acquiring them.

Compounding the lack of variety and accessibility problems surrounding these specialty bandages is the recent and widespread proliferation of home computers and the internet to which young people in particular are attracted at the expense of learning traditional life skills, including the dressing and care for cuts and other wounds.

There therefore exists a need in the bandage art for greater flexibility in the selection of the fanciful graphics which may adorn a given bandage, as well as a system through which younger children may relate traditional life skills with the technology that interests them and pervades much of their lives.

With the forgoing problems and concerns in mind, it is the general object of the present invention to provide an ink jet printable bandage which overcomes the above-described concerns and drawbacks, and which captures the imagination of young minds and their fascination with commonly available technology.

SUMMARY OF THE INVENTION

It is an object of the present invention to provide a bandage capable of having numerous, fanciful graphics printed thereon.

It is another object of the present invention to provide a bandage wherein the fanciful graphics printed thereon are selected by an operator.

It is another object of the present invention to enable an operator to select the graphic to be printed from a predetermined set of graphics, a graphic which has been personally designed or a graphic downloaded from the internet.

It is another object of the present invention to utilizes a personal printer to print the desired graphics on the bandage.

It is another object of the present invention to provide a special film on a bandage which will bond with the commercially available ink utilized in home printers.

It is another object of the present invention to provide a special film on a bandage which will bond to the commercially available ink in home computers in a waterproof manner.

It is another object of the present invention to stimulate children's interest in the care of wounds by incorporating technology based applications.

According to one embodiment of the present invention a bandage is adapted to receive a printed graphic image which is printed by a personal home printer. The predetermined graphic image may be chosen from a graphics library loaded onto a personal computer, a graphic image designed by an operator or a graphic image downloaded from the internet. The bandage includes a first layer treated with a coating on one planar side, the coating bonding with the printed graphic image in a water-proof manner. The bandage further includes a second pressure sensitive adhesive layer disposed on another planar side of the first layer, and a third liner layer which overlays the second adhesive layer. The third liner layer is selectively removable from the second adhesive layer to expose the second adhesive layer.

These and other objectives of the present invention, and their preferred embodiments, shall become clear by consideration of the specification, claims and drawings taken as a whole.

DETAILED DESCRIPTION OF THE PREFERRED EMBODIMENT

Figure 1:
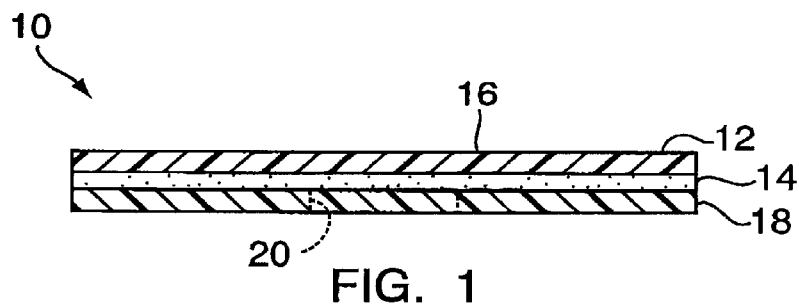
FIG. 1 is a cross-sectional view of an ink jet printable bandage, according to one embodiment of the present invention.

FIG. 1 is a cross sectional view of an ink jet printable bandage 10, according to one embodiment of the present invention. As depicted in FIG. 1, the bandage 10 includes a first film layer 12 and a second adhesive layer 14. The film layer 12 is designed to be the exterior, or exposed, portion of the bandage 10 when the bandage 10 is applied to a wound. The film layer 12 includes a water-proof ink jet coating 16 which is formed, deposited or otherwise impregnated onto the film layer 12.

The coating 16 may have any chemical composition provided that the coating 16 is capable of bonding with the ink utilized by printers, preferably home printers, so that any graphic printed thereon becomes bonded to the coating 16 in such a manner as to be rendered water insoluble or waterproof, as will be described in more detail later. It will be readily appreciated that the film layer 12 may be chosen from any known, elastic or semi-elastic bandage material, such as cloth, plastic, mesh or the like, without departing from the broader aspects of the present invention.

Returning to FIG. 1, the adhesive layer 14 is formed, deposited or otherwise fixed to a planar surface of the film layer 12, opposite to the planar surface upon which the coating 16 is formed. The adhesive layer 14 is comprised of an acrylic, skin-friendly pressure sensitive adhesive which, in turn, is protected from exposure or premature contact via a liner 18. As will be understood by one of ordinary skill in the art, the liner 18 may be a silicone coated release liner, or the like, which may be selectively removed, in whole or in part, to expose the adhesive layer 14 beneath, typically at a time immediately prior to the application of the bandage 10. Moreover, the pressure sensitive adhesive is not limited to an acrylic-based adhesive, rather the present invention contemplates any known adhesive capable of releasably bonding with human skin or the like.

The bandage 10 of the present invention further includes a perforated pad area 20, shown in hidden lines in FIG. 1. The pad area 20 is selectively removable from the bandage 10 and provides an anchoring location for the positioning of a wound pad, such as but not limited to a non-adherent, absorbent pad or the like, for contacting the wound area when the bandage 10 is applied to the wound. As will be appreciated, by selectively removing the pad area 20, a portion of the adhesive layer 14 will be exposed and a wound pad may be subsequently applied thereto.

As described in conjunction with FIG. 1, an important aspect of the present invention is the formation of the bandage 10 which includes the coating 16, thereby enabling the imprinting of a selected graphic onto the bandage 10 and the water-proof bonding of any such printed graphic to the coating 16. In the preferred embodiment, a plurality of the bandages 10 would be formed upon a common bandage sheet for insertion into a printing apparatus, such as but not limited to a home ink jet or bubble printer.

Figure 2:
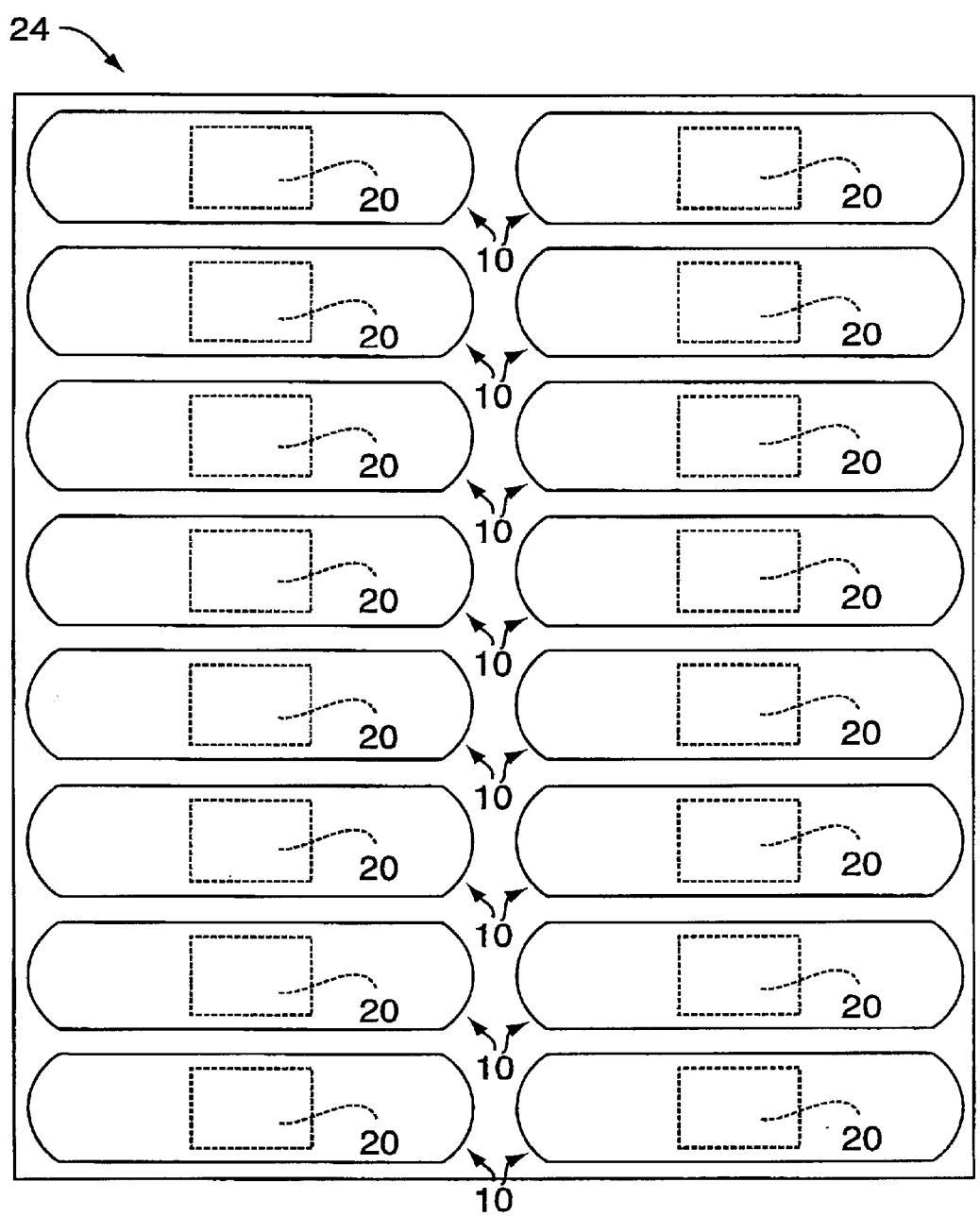
FIG. 2 is a planar view of a bandage sheet illustrating the arrangement of a plurality of bandages as depicted in FIG. 1.

FIG. 2 depicts one such bandage sheet 24 according to one embodiment of the present invention. As depicted in FIG. 2, a plurality of bandages 10 are formed on a common bandage sheet 24 by cutting the desired shape of the bandages 10 into the bandage sheet 24; that is, by perforating the bandage sheet 24 from the film layer 12 through the liner layer 18 in a manner which does not compromise the integrity of the bandage sheet 24. Likewise, the pad area 20 may be formed in each of the bandages 10 of the bandage sheet 24 by perforating only the liner layer 18. It will be readily appreciated that the bandages 10 and the pad areas 20 may be of any shape or size without departing from the broader aspects of the present invention.

In the preferred embodiment of the present invention, the bandage sheet 24 of FIG. 2 is dimensioned to be approximately 8.5"×" for easy application with commercially available home printers, however the present invention contemplates bandage sheets 24 of any dimension having any number of bandages 10 formed thereon.

It is another important aspect of the present invention that an operator may design bandages having graphic images printed thereon whereby the images may be chosen from a predetermined catalog of stored images or, alternative, may allow the operator design of original images or the downloading of images from the internet, as will now be described in conjunction with FIG. 3.

Figure 3:
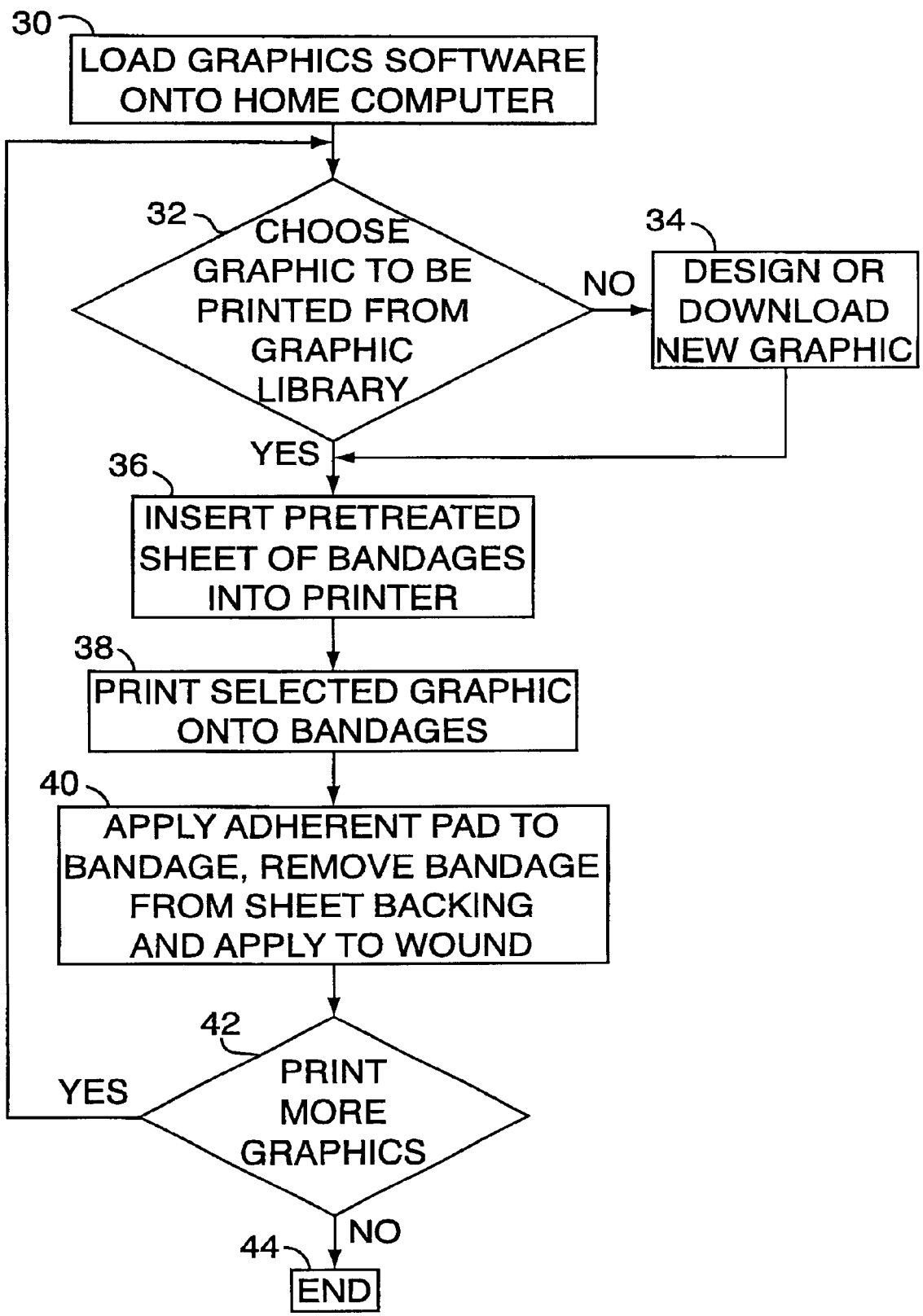
FIG. 3 is a flow diagram illustrating the steps involved in one embodiment of a bandage printing process.

As depicted in step 30 of FIG. 3, an operator would load a graphics software program onto a personal home computer. The graphics program would include a graphics library containing a predetermined number of pre-designed graphic images to chose from, such as but not limited to geometric specific type of injury, such as 'scratch' or the like, or scenes relating to special events and traditional holidays. In addition, the graphics program may include prompts as to the size of the bandage sheet 24, the number and shape of the bandages 10 on the bandage sheet 24 and may further include a child-friendly animated character to tutor an operator through the selection and imprinting process.

In step 32, an operator would be prompted to select one of the predetermined graphic images to be imprinted, while step 34 allows an operator to design their own image should none of the predetermined graphic images in the graphics library be desired. The design of a unique or customized graphic image may be accomplished utilizing a graphic workshop program imbedded within the graphic software program. Moreover, as depicted in FIG. 3, step 34 includes the ability to download graphic images from the internet as an alternative to creating a new graphic utilizing the loaded graphics program. In the preferred embodiment of the present invention, the graphics software program would facilitate the acquisition of a graphic image from an internet connection.

In step 36, an operator would load the appropriately sized bandage sheet 24 into a home printer which is in data communication with the home computer.

The printing of the chosen graphic image is then accomplished in step 38. It will be readily appreciated that the loaded graphics program may include the ability to print more than one graphic image on a given bandage sheet 24, or to print a common graphic image having differing color schemes for each bandage 10 on the bandage sheet 24, without departing from the broader aspects of the present invention.

As depicted in step 40, subsequent to printing the chosen graphic image onto the bandage sheet, an operator remove the perforated pad area 20 on a given bandage 10 and apply a wound pad thereto, thus resulting in a prepared bandage. As further depicted in step 40, the operator would then disengage the entirety of the prepared bandage from the bandage sheet 24 and subsequently removes the remaining liner layer 18 so as to expose the adhesive layer 14. Application of the prepared bandage to the wound site would then be accomplished in a well-known manner.

In step 42, the operator is prompted to determine if another printing of graphic images will be performed, whereby the graphics selection and printing process is begun once again, if desired, or alternatively the graphics program will end in step 44.

It will be readily appreciated that the flow diagram of FIG. 3 describes the general operation of the graphics program in conjunction with the bandages 10, however minor modifications in the order of the steps depicted in FIG. 3 are contemplated as well. For example, the insertion of the bandage sheet 24 in step 36 may be accomplished prior to the selection or design of the graphic image to be printed in steps 32 and 34. Likewise, the preparation of a given bandage 10 in step 40 may be delayed until after the graphics program ends in step 44, without departing from the broader aspects of the present invention.

As described above in conjunction with FIGS. 1–3, subsequent to the graphic image being imprinted upon the coating 16 of the film layer 12 and the wound pad being applied to the pad area 20, the entirety of the liner layer 18 will be removed to expose the adhesive layer 14 for adhesion to the skin of a patient. The present invention is not so limited in this regard as the architecture of the bandage may be modified without departing from the broader aspects of the present invention.

Figure 4:
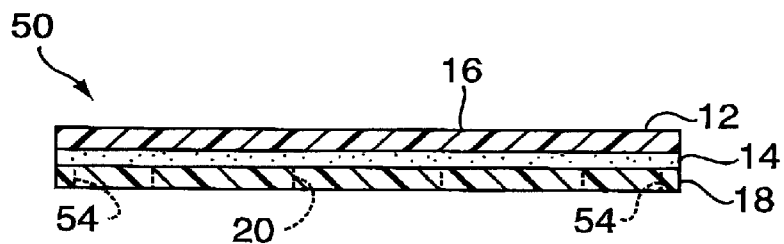
FIG. 4 is a cross-sectional view of an ink jet printable bandage, according to another embodiment of the present invention.

As depicted in FIG. 4, a bandage 50 includes the first film layer 12 and the second adhesive layer 14. Similar to the bandage 10 depicted in FIG. 1, the film layer 12 is designed to be the exterior, or exposed, portion of the bandage 50 when the bandage 50 is applied to a wound, while the film layer 12 includes the water-proof ink jet coating 16 which is formed, deposited or otherwise impregnated onto the film layer 12. The bandage 50 also includes a perforated pad area 20 for securing a wound pad thereon.

Figure 5:
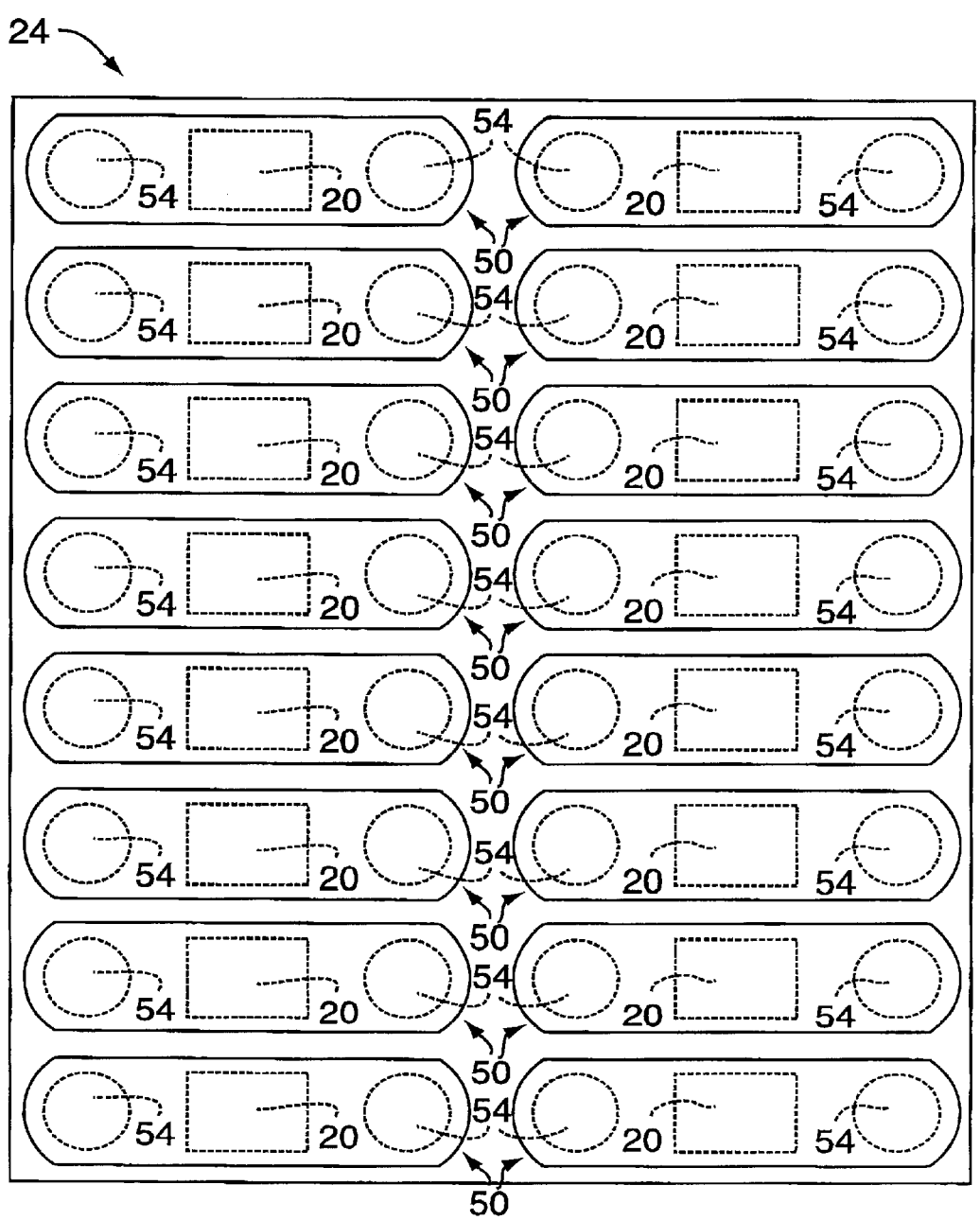
FIG. 5 is a planar view of a bandage sheet illustrating the arrangement of a plurality of bandages as depicted in FIG. 4.

In contrast to the bandage 10 depicted in FIG. 1, the bandage 50 of FIG. 4 includes a pair of attachment areas 54 which are themselves delineated by perforations through the liner layer 18. In implementation, the attachment areas 54 would be removed to expose the adhesive layer 14 at locations adjacent the distal ends of the bandage 50, while leaving the remainder of the liner layer 18 intact, with the exception of the pad area 20, as described previously. FIG. 5 illustrates a bandage sheet 56 which has a plurality of the bandages 50 impregnated thereon.

As depicted in the embodiments of FIGS. 1–5, the present invention enables the customization of bandages with fanciful graphic images not limited by the predetermined selection of a third party manufacturer. Moreover, by combining computer and internet technology with the preparation and use of bandages, the likelihood of children's interest in wound care, and their education in the use of new technology, increases. Moreover, by advantageously treating the exterior surface of the bandage with a waterproof coating capable of bonding with the ink from home computers and the like, the present invention permits the manufacture of commercial-grade quality bandages in a home setting.

While the invention had been described with reference to the preferred embodiments, it will be understood by those skilled in the art that various obvious changes may be made, and equivalents may be substituted for elements thereof, without departing from the essential scope of the present invention. Therefore, it is intended that the invention not be limited to the particular embodiments disclosed, but that the invention includes all embodiments falling within the scope of the appended claims.

What is claimed is:

1. A method for customizing a bandage having an ink-bondable coating on an exterior surface thereof by printing a graphic image on said exterior surface utilizing a personal home computer and printer, said method comprising the steps of:

orienting a bandage sheet in said home printer, said bandage sheet including said bandage defined by a perforated perimeter about an entirety of said bandage;

selecting said graphic image to be imprinted upon said bandage; and printing said graphic image onto said ink-bondable coating wherein said printed graphic image bonds with said ink-bondable coating in a water-proof manner.

2. The method for customizing a bandage according to claim 1, wherein said selecting step includes:

loading a graphics software package onto said home computer, said graphics program comprising a graphics library having a plurality of pre-designed graphic images; and choosing one of said plurality of pre-designed graphic images to be printed upon said bandage.

3. The method for customizing a bandage according to claim 1, wherein said selecting step includes:

loading a graphics software package onto said home computer, said graphics program comprising a graphics workshop program for designing a plurality of customized graphic images; and choosing one of said plurality of customized graphic images to be printed upon said bandage.

4. The method for customizing a bandage according to claim 1, wherein said selecting step includes:

loading a graphics software package onto said home computer, said graphics program facilitating an acquisition of a downloaded graphic image from an internet connection; and choosing said downloaded graphic image to be printed upon said bandage.

5. The method for customizing a bandage according to claim 1, wherein said printing step includes:

communicating the size of said bandage sheet to said graphics software program.

6. The method for customizing a bandage according to claim 1, further comprising the steps of:

forming a plurality of bandages on said bandage sheet; and communicating the number of bandages defined on said bandage sheet to said graphics software program.

7. The method for customizing a bandage according to claim 1, further comprising the steps of:

removing said bandage sheet from said printer subsequent to said graphic image being printed onto said ink-bondable coating;

disengaging said bandage from said bandage sheet;

removing a portion of a liner of said bandage thereby exposing an adhesive layer of said bandage and forming a wound pad area; and fixing a wound pad on said wound pad area by pressing said wound pad onto said exposed adhesive layer.

8. A method for customizing a bandage having an ink-bondable coating on an exterior surface thereof by printing a graphic image on said exterior surface utilizing a personal home computer and printer, said method comprising the steps of:

orienting a bandage sheet in said home printer, said bandage sheet including said bandage being defined thereon;

selecting said graphic image to be imprinted upon said bandage; and printing said graphic image onto said ink-bondable coating wherein said printed graphic bonds with said ink-bondable coating in a water-proof manner.

* * * * *